US012649659B2

(12) United States Patent
Cheng et al.

(10) Patent No.: US 12,649,659 B2
(45) Date of Patent: Jun. 9, 2026

(54) METHOD FOR RECOVERING RAW AND AUXILIARY MATERIALS IN THE PRODUCTION OF LITHIUM BIS(FLUOROSULFONYL)IMIDE

(71) Applicants: CONTEMPORARY AMPEREX TECHNOLOGY CO., LIMITED, Ningde (CN); CATL-SICONG NOVEL MATERIALS CO., LTD, Longyan City (CN)

(72) Inventors: Sicong Cheng, Longyan City (CN); Qisen Huang, Ningde (CN)

(73) Assignees: CONTEMPORARY AMPEREX TECHNOLOGY CO., LIMITED, Ningde City (CN); CATL-SICONG NOVEL MATERIALS CO., LTD., Longyan City (CN)

( * ) Notice: Subject to any disclaimer, the term of this patent is extended or adjusted under 35 U.S.C. 154(b) by 544 days.

(21) Appl. No.: 18/364,732

(22) Filed: Aug. 3, 2023

(65) Prior Publication Data

US 2024/0017999 A1 Jan. 18, 2024

Related U.S. Application Data

(63) Continuation of application No. PCT/CN2022/074936, filed on Jan. 29, 2022.

(51) Int. Cl.

*C01B 21/086* (2006.01)
*B01D 3/14* (2006.01)
(Continued)

(52) U.S. Cl.

CPC ............ *C01B 21/086* (2013.01); *B01D 3/148* (2013.01); *B01D 5/006* (2013.01);
(Continued)

(58) Field of Classification Search

CPC ... C01B 21/086; C01B 21/0935; B01D 3/148; B01D 5/006; B01D 17/0217;
(Continued)

(56) References Cited

U.S. PATENT DOCUMENTS

2012/0020867 A1 1/2012 Morinaka et al.

FOREIGN PATENT DOCUMENTS

CN 102378755 A * 3/2012 .......... B01J 31/0252
CN 106543009 A 3/2017
(Continued)

OTHER PUBLICATIONS

ISR for International Application PCT/CN2022/074936 mailed Oct. 25, 2022.
(Continued)

*Primary Examiner* — Anthony J Zimmer
*Assistant Examiner* — Jaanzeb C Raja
(74) *Attorney, Agent, or Firm* — Ladas & Parry LLP

(57) ABSTRACT

A method for recovering raw and auxiliary materials in the production of lithium bis(fluorosulfonyl)imide is described. The method includes one or more different recovery sections A, B, C, D and/or E, corresponding to the recovery and post-treatment of the raw and auxiliary materials such as triethylamine, a fluoride ion, an ester solvent, and a crystallization liquid respectively used in the production of lithium bis(fluorosulfonyl)imide. The method for recovering raw and auxiliary materials of the present application enables the production of lithium bis(fluorosulfonyl)imide to have significantly improved economic efficiency and environmental protection.

19 Claims, 3 Drawing Sheets

(51) Int. Cl.

| | |
|---|---|
| ***B01D 5/00*** | (2006.01) |
| ***B01D 17/02*** | (2006.01) |
| ***B01D 17/04*** | (2006.01) |
| ***C07C 17/392*** | (2006.01) |
| ***C07C 68/08*** | (2006.01) |
| ***C07C 209/86*** | (2006.01) |

(52) U.S. Cl.
CPC ....... *B01D 17/0217* (2013.01); *B01D 17/045* (2013.01); *C07C 17/392* (2013.01); *C07C 68/08* (2013.01); *C07C 209/86* (2013.01)

(58) Field of Classification Search
CPC ..... B01D 17/045; C07C 17/392; C07C 68/08; C07C 209/86; Y02E 60/10; H01M 10/0525; C01D 3/02
See application file for complete search history.

(56) References Cited

FOREIGN PATENT DOCUMENTS

| | | | | |
|---|---|---|---|---|
| CN | 107188138 A | | 9/2017 | |
| CN | 109369419 A | * | 2/2019 | ........... C07C 209/82 |
| CN | 110155967 A | | 8/2019 | |
| CN | 110436424 A | | 11/2019 | |
| CN | 111620315 A | | 9/2020 | |
| CN | 111792630 A | | 10/2020 | |
| CN | 113336793 A | | 9/2021 | |
| CN | 113511639 A | | 10/2021 | |
| GB | 803552 A | | 10/1958 | |
| WO | 2018104674 A1 | | 6/2018 | |
| WO | 2019229365 A1 | | 12/2019 | |

OTHER PUBLICATIONS

Written Opinion for International Application PCT/CN2022/074936 mailed Oct. 25, 2022.
First Chinese Office Action for copending application 202210111633.4 mailed Jun. 9, 2022.
Second Chinese Office Action for copending application 202210111633.4 mailed Nov. 23, 2022.
Huang Taisan et al., Comprehensive Utilization of Waste, Fujian Science and Technology Press, 1998, p. 11-12.
Hong Zhongling, ed., Deep Processing of Chemical Organic Raw Materials, Chemical Industry Press, Jun. 1997, p. 137.

* cited by examiner

METHOD FOR RECOVERING RAW AND AUXILIARY MATERIALS IN THE PRODUCTION OF LITHIUM BIS(FLUOROSULFONYL)IMIDE

CROSS REFERENCE OF RELATED APPLICATIONS

This application is a continuation of International Patent Application No. PCT/CN2022/074936, filed on Jan. 29, 2022. The aforementioned patent application is incorporated by reference in its entirety.

TECHNICAL FIELD

The present application relates to a method for recovering raw and auxiliary materials in the production of lithium bis(fluorosulfonyl)imide, in particular to a method for recovering triethylamine, a fluoride, an ester solvent, a crystallization liquid and/or a waste gas containing dichloromethane in a waste liquid produced in the production of lithium bis(fluorosulfonyl)imide through different recovery sections.

BACKGROUND

Lithium bis(fluorosulfonyl)imide (of which chemical formula is $Li[N(SO_2F)_2]$, English abbreviation is LiFSI) is an important new material containing fluorine. Due to a special molecular structure, LiFSI has a low binding energy between $Li^+$ and $FSI^-$, which is conducive to the dissociation of $Li^+$. Therefore, by adding LiFSI to an electrolytic solution, higher conductivity can be obtained. Meanwhile, LiFSI also has characteristics of high thermal stability, wide electrochemical window, and low corrosion rate, especially in a power battery, it can improve cycle performance and rate performance of the power battery, and is expected to become a new electrolyte lithium salt for lithium-ion batteries. In 2012, Nippon Shokubai demonstrated LiFSI for the first time, and realized industrial production in 2013. At present, Japanese and Korean battery companies have mixed LiFSI and $LiPF_6$ in high-end occasions.

At present, reason why LiFSI cannot be used on a large scale is mainly due to high production costs resulted from the limitation of synthesis process conditions. In a synthesis process, there are shortcomings such as cumbersome process, long procedure, low product conversion rate, large energy consumption and environmental pollution. In addition, as an electrolyte for a lithium-ion secondary battery, LiFSI needs to meet demanding requirements such as high purity and anhydrous property. In particular, after the introduction of water, it is difficult to completely remove the water by heating-up and drying till decomposition, and even if the water is removed, a great loss in yield is required.

In addition, in the process of industrial synthesis and purification of LiFSI, it is necessary to fully recycle raw and auxiliary materials used, and reduce the generation of three wastes (waste water, waste gas and solid waste) as much as possible.

SUMMARY

The present application is made in view of the above problems, and an object thereof is to provide a method for recovering raw and auxiliary materials in the production of lithium bis(fluorosulfonyl)imide, in order to enhance the degree of recovering the raw and auxiliary materials in the production of lithium bis(fluorosulfonyl)imide and improve economic efficiency and environmental protection of the lithium bis(fluorosulfonyl)imide production.

In order to achieve the above object, a first aspect of the present application provides a method for recovering raw and auxiliary materials in the production of lithium bis(fluorosulfonyl)imide, the production of lithium bis(fluorosulfonyl)imide including reaction 1 of subjecting sulfuryl fluoride, triethylamine and ammonia gas to reaction and subsequent reaction 2 of alkalinizing a reaction product, reaction 1

$$SO_2F_2 + NH_3 + Et_3N \longrightarrow (SO_2F{-}NH{-}SO_2F)\cdot Et_3N + Et_3N\cdot(HF)_n \quad (n = 1\text{-}12),$$

and reaction 2

$$(SO_2F{-}NH{-}SO_2F)\cdot Et_3N + LiOH \longrightarrow (SO_2F{-}N{-}SO_2F)^{-}Li^{+} + Et_3N + H_2O,$$

where the method includes:

a recovery section A: separating a product mixture produced by reaction 1 into an oil phase including $(SO_2F{-}NH{-}SO_2F)\cdot Et_3N$ and an aqueous phase including a triethylamine hydrogen fluoride salt and impurity ions; subjecting the oil phase including $(SO_2F{-}NH{-}SO_2F)\cdot Et_3N$ to an alkalinization process according to reaction 2, and introducing the aqueous phase including the triethylamine hydrogen fluoride salt and the impurity ions into an alkalinization kettle to mix and react with an alkali metal hydroxide under stirring, and then introducing a solution obtained after reaction in the alkalinization kettle into a layered tank for phase separation, with an upper layer oil phase being an organic phase including water and triethylamine, which is separated out and stored in an oil phase secondary layered tank; and a recovery section B: passing a product mixture obtained by the alkalinization process according to reaction 2 through an evaporator to remove the triethylamine and part of the water, and introducing the evaporated triethylamine and water into a condenser for condensation and standing for liquid separation; transferring an upper layer triethylamine solution obtained after the liquid separation to a triethylamine transfer tank, to be separated into an aqueous phase and an oil phase through a centrifuge, the oil phase being an organic phase including water and triethylamine; introducing the organic phase and the organic phase including the water and the triethylamine obtained in the recovery section A together into a single-effect evaporation system to obtain a water-containing triethylamine phase; then removing remaining water by dehydration in a dehydration tower and rectification in a rectification tower respectively to obtain high-purity triethylamine.

In any embodiment, the recovery method is a part of a complete process for the production and purification of lithium bis(fluorosulfonyl)imide, and includes a plurality of recovery sections corresponding to the separation and recovery of different raw and auxiliary materials. There may also be material exchange and combination between recovery sections.

In any embodiment, purity of the high-purity triethylamine obtained by the method is above 95 wt %; optionally, the purity is above 98 wt %, above 99 wt % or above 99.5 wt %. In any embodiment, the product mixture obtained by the alkalinization process in the recovery section B is evaporated by the evaporator to obtain a mixture including triethylamine and water, and the mixture is condensed in a condenser, and then heated to a temperature of 30° C.-55° C. to stand for layering. In any embodiment, the product mixture produced by reaction 1 in the recovery section A is subjected to layering by a static mixer or extraction by an extraction tower.

In any embodiment, a lower layer aqueous phase obtained by phase separation in the layered tank of the recovery section A mainly includes an alkali metal fluoride solution and a small amount of triethylamine, and is combined with a lower layer aqueous phase obtained in the single-effect evaporation system, the dehydration tower and the rectification tower in the recovery section B in a brine tank; after a liquid in the brine tank is introduced into a stripping tower for stripping, a light phase obtained mainly includes triethylamine and water, which are returned to the oil phase secondary layered tank of the recovery section A; and a heavy component obtained after stripping mainly includes the alkali metal fluoride solution, and the heavy component is introduced into a double-effect evaporator for evaporation to obtain a high-concentration alkali metal fluoride solution. In any embodiment, an alkali metal is Li, Na or K.

In any embodiment, the production of lithium bis(fluorosulfonyl)imide further includes a dehydration process performed by using an ester solvent, and a water-containing ester solvent evaporated by evaporation is recovered by a recovery section C: introducing the water-containing ester solvent into an ester solvent buffer tank to be mixed with a lithium hydroxide solution in a pipeline mixer, and then separated by a coalescing separator, to obtain an oil phase of the ester solvent in a large proportion after separation, and introducing the oil phase into an ester solvent storage tank. Further, an aqueous phase obtained after the separation of the coalescing separator is added with a lithium hydroxide solution to adjust a pH value, and then enters a stripping tower through a preheater for stripping, to obtain an oil phase of the water-containing ester solvent, which is returned to the ester solvent buffer tank; and an aqueous phase and a residual liquid obtained are introduced into a sewage treatment device for post-treatment.

In any embodiment, the ester solvent includes ethyl methyl carbonate EMC, diethyl carbonate DEC and dimethyl carbonate DMC.

In any embodiment, the production of lithium bis(fluorosulfonyl)imide further includes a crystallization process in which a crystallization liquid is used to dissolve an ester solvent and precipitate product LiFSI crystals, and a crystallization liquid washing oil phase separated includes dichloromethane, an ester solvent, water and a salt; and the crystallization liquid is recovered by a recovery section D: introducing the crystallization liquid washing oil phase into a dehydration tower, where a condensate on the top of the tower includes dichloromethane and water, and an upper layer aqueous phase after layering is introduced into a sewage collection tank for post-treatment, and a lower layer dichloromethane all flows back; introducing a tower bottom liquid of the dehydration tower into a single-effect evaporation system, introducing a gas phase obtained by evaporation into a rectification tower for rectification, obtaining dichloromethane from a condensate on the top of the rectification tower, collecting the dichloromethane in a dichloromethane blending tank, adding lithium hydroxide to the tank, and adjusting a pH value through a pump circulation pipeline and separating phases, so that an aqueous phase obtained is separated for post-treatment, and an oil phase obtained is introduced into a dichloromethane storage tank.

In any embodiment, ethanol is separated from the middle of the rectification tower for post-treatment; an ester solvent is obtained from a condensate in the middle and lower part of the rectification tower, and the ester solvent is introduced into an ester solvent storage tank for reuse in a dehydration process; and a residual liquid obtained from the bottom of the rectification tower is separated for post-treatment.

In any embodiment, a liquid phase obtained from the single-effect evaporation system is subjected to vacuum concentration, and a condensate obtained includes dichloromethane and an ester solvent, and is sent back to the dehydration tower; and the condensate obtained after vacuum concentration is separated for post-treatment.

In any embodiment, the method further includes a recovery section E for recovering a waste gas containing dichloromethane generated in each stage, the recovery section E including: cooling the waste gas containing dichloromethane generated in each stage to be introduced into a three-stage adsorption resin for adsorption, using steam for desorption after the adsorption is saturated, and then performing collection through condensation, where a liquid containing dichloromethane and water obtained by the collection is left to stand for layering, an upper layer aqueous phase contains a minute amount of dichloromethane, and is separated as waste water for post-treatment; and a lower layer oil phase is dichloromethane containing a minute amount of water, and is introduced into a dehydration device for dehydration and then reused.

In any embodiment, a water content in the dichloromethane containing the minute amount of water is 1000-2000 ppm, and the dehydration is performed until the water content is 50-200 ppm. In any embodiment, the dehydration is performed through a 4A molecular sieve.

By means of the method for recovering raw and auxiliary materials as described above, at least one or more raw and auxiliary materials used in the production of lithium bis(fluorosulfonyl)imide can be recovered in a plurality of different recovery sections, and post-treatment is performed on three waste materials produced, thereby enabling the production of lithium bis(fluorosulfonyl)imide to have significantly improved economic efficiency and environmental friendliness.

BRIEF DESCRIPTION OF THE DRAWINGS

To illustrate technical solutions of the present application more clearly, a brief introduction on the accompanying drawings which are needed in embodiments of the present application will be given below. Obviously, the accompanying drawings described below are merely some of the embodiments of the present application, based on which other drawings may be obtained by those of ordinary skill in the art without any creative effort.

DETAILED DESCRIPTION

Figure 1:
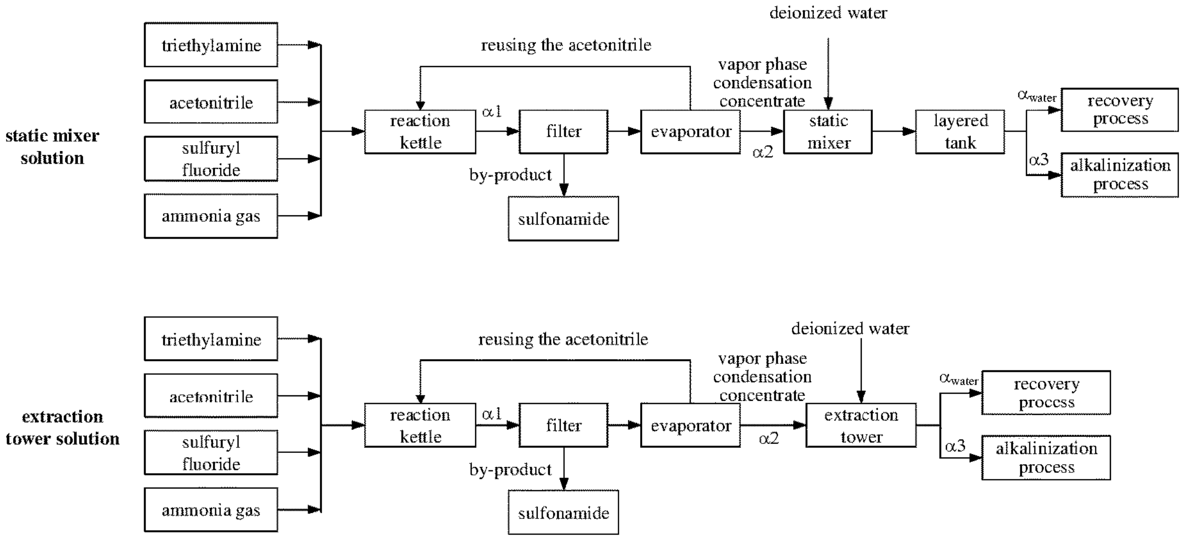
FIG. 1 is a schematic process flow diagram of an a stage of a process for producing lithium bis(fluorosulfonyl)imide in an embodiment of the present application.

For the sake of brevity, the present application specifically discloses some numerical ranges. However, any lower limit may be combined with any upper limit to form a range that is not expressly recited; and any lower limit may be combined with another lower limit to form a range that is not expressly recited, and likewise any upper limit may be combined with any other upper limit to form a range that is not expressly recited. Furthermore, each individually disclosed point or individual value may serve as a lower or upper limit in combination with any other point or individual value or with other lower or upper limit to form a range that is not expressly recited.

Due to a special molecular structure, lithium bis(fluorosulfonyl)imide (LiFSI) can be added to an electrolytic solution to obtain higher conductivity. Meanwhile, LiFSI also has characteristics of high thermal stability, wide electrochemical window, and low corrosion rate. In particular, in a power battery, it can improve cycle performance and rate performance of the power battery, and thus is an excellent choice of an electrolyte lithium salt for a lithium-ion battery. Synthesis and purification of LiFSI in the prior art have many problems in industrial large-scale production, for example, a cumbersome synthesis process, a long process, a low conversion rate of product, and large consumption of raw and auxiliary materials and recovery difficulty, and therefore economic efficiency is not high. The present invention aims to solve at least some of these problems and provides a new process of producing LiFSI and method for recovering raw and auxiliary materials.

The process of producing LiFSI mainly includes the following steps.

Synthesis: sulfuryl fluoride, ammonia gas, and triethylamine are fully mixed so that the sulfuryl fluoride and the ammonia gas fully react, while the triethylamine acts as a solvent and participates in the reaction. Other organic solvents, such as acetonitrile, can also be used as a solvent for the reaction. The main reaction is $SO_2F_2+NH_3+Et_3N \rightarrow (SO_2F—NH—SO_2F)\cdot Et_3N+Et_3N\cdot(HF)_n$(n=1-12).

When temperature in a reaction kettle is too high, the following side reaction will take place and affect yield: $NH_3+SO_2F_2+Et_3N \rightarrow NH_2—SO_2—NH_2$ (sulfonamide, solid)+$Et_3N\cdot(HF)_n$ (triethylamine hydrogen fluoride salt soluble in $CH_3CN$, where n=1-12). After the reaction, a by-product sulfonamide solid can be filtered out by using a 5 m tetrafluoro filter bag for example.

After the synthesis process, material composition mainly includes $(SO_2F—NH—SO_2F)\cdot Et_3N$, acetonitrile, triethylamine hydrogen fluoride salt, triethylamine (a small amount) and impurity ions. The impurity ions mainly include $F^-$, $SO_4^{2-}$, $FSO_3^-$ and $Cl^-$.

Evaporation: a product mixture (a material α1) is introduced into an evaporator for evaporation, and the acetonitrile solvent is separated out. A falling film evaporator can be used to heat the material, a gas-liquid separator can be used to separate a liquid from a vapor, and a condenser can be used to condense the vapor of acetonitrile (containing a small amount of triethylamine), which can be reused for the first step of synthesis.

After the evaporation process, the material composition mainly includes $(SO_2F—NH—SO_2F)\cdot Et_3N$, triethylamine hydrogen fluoride salt, acetonitrile (a minute amount) and impurity ions.

Extraction: a concentrate (a material α2) obtained by evaporation is washed with water to remove water-soluble impurities (mainly the triethylamine hydrogen fluoride salt). Hereby, two solutions can be used.

Solution 1, an extraction tower, in which a light phase (low density) enters from the bottom, the light phase exits from the upper part, a heavy phase enters from the top, and the heavy phase exits from the bottom, and the middle is stirred in a spiral shape; and solution 2, a static mixer and a phase separation tank. An extracted oil phase (a material α3) mainly includes $(SO_2F—NH—SO_2F)\cdot Et_3N$, while an extracted aqueous phase (a material α water) mainly includes triethylamine hydrogen fluoride salt and impurity ions (such as $F^-$, $SO_4^{2-}$, $FSO_3^-$, and $Cl^-$). In some embodiments, an extraction tower is used for extraction to achieve better separation of the impurity ions (such as $F^-$). In some embodiments, a content of an impurity ion in the oil phase obtained by the extraction with the static mixer is 5-30 times greater than the content of the impurity ion in the oil phase obtained by the extraction with the extraction tower, optionally 10-20 times. Optionally, the impurity ion is $F^-$. In the production of lithium bis(fluorosulfonyl)imide of the present application, a stage of synthesis-evaporation-extraction is called an a stage, and a specific process thereof can refer to a process flow chart in FIG. 1 of the present application.

Alkalinization: the extracted oil phase (the material α3) obtained after extraction is mixed with a lithium hydroxide aqueous solution for full reaction. The reaction is reaction 2: $(SO_2F—NH—SO_2F)\cdot Et_3N+LiOH \rightarrow (SO_2F—N—SO_2F)^- Li^++Et_3N+H_2O$. The reaction principle is that a strong base replaces a weak base, the alkalinity of LiOH is stronger than that of triethylamine in $(SO_2F—NH—SO_2F)\cdot Et_3N$, so that triethylamine is replaced. Triethylamine is removed by falling film evaporation, and LiOH reacts with $(SO_2F—NH—SO_2F)\cdot Et_3N$ at the same time to generate a lithium salt (lithium bis(fluorosulfonyl)imide, abbreviated as LiFSI).

Dehydration: a reaction mixture (a material β1) obtained in reaction 2 is dehydrated using an evaporator. An ester solvent is used to carry water, and no chemical reaction is involved. Because a lithium salt is very strong in water absorption, it is unrealistic to reduce a water content to a desired requirement simply by evaporation. Replenishing a large amount of ester solvents can weaken the adsorption of the lithium salt to water, and the water content can be reduced to the desired requirement during the process of evaporating the ester solvent while replenishing the ester solvent. The ester solvent can be reused after purification treatment in a recovery section. The ester solvent may include ethyl methyl carbonate (EMC), diethyl carbonate (DEC), dimethyl carbonate (DMC) and the like. During the dehydration process, $(SO_2F—N—SO_2F)^-Li^+$ is also decomposed to generate by-products LiF, $Li_2SO_4$, lithium sulfamate, etc. The solid by-products should be filtered or centrifuged before the subsequent desolventization process (for example, solid residues are remove by means of centrifugation and sedimentation, such as a scraper centrifuge or a disc centrifuge).

Figure 2:
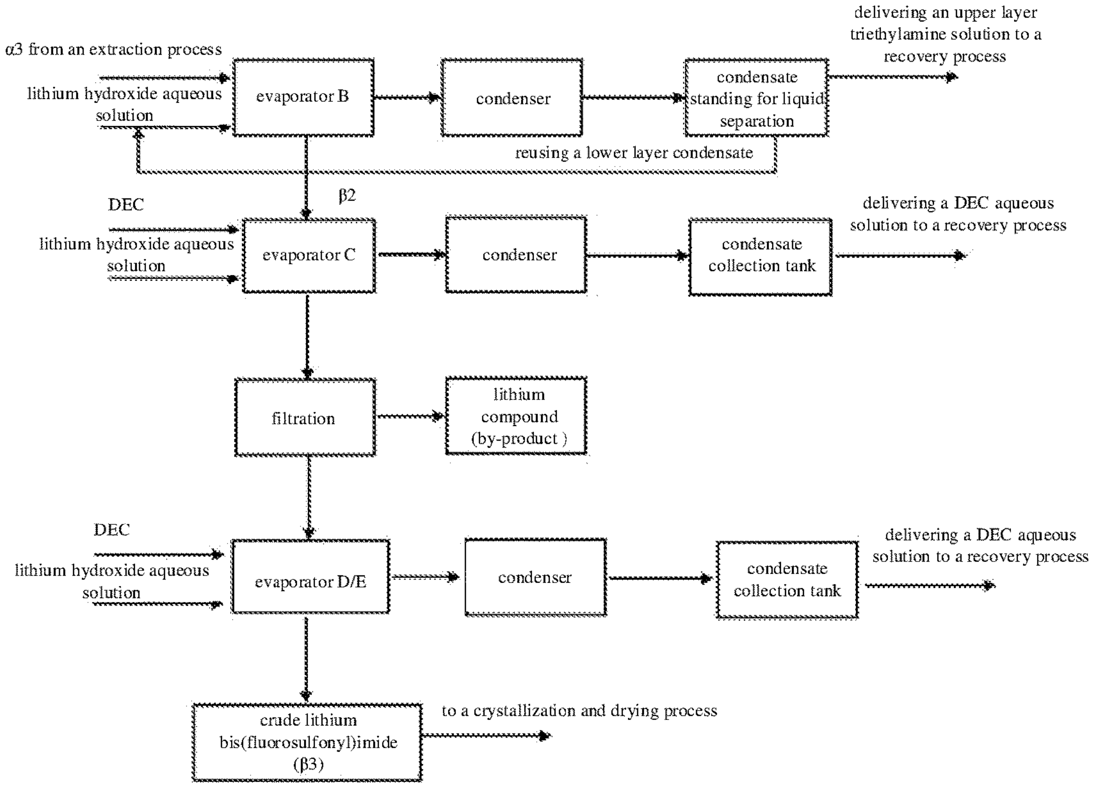
FIG. 2 is a schematic process flow diagram of a R stage of a process for producing lithium bis(fluorosulfonyl)imide in an embodiment of the present application.

Desolventization: a material (a material β2) obtained after evaporation and dehydration is desolvated in an evaporator. Desolventization does not involve a reaction, but simply aims to evaporate the ester solvent. Given that the lithium salt is dissolved in the ester solvent, if the ester solvent is not evaporated to a certain extent (such as from 60%-65% to 30%), crystallization will not be able to be performed or a crystallization rate will be very low in the later stage. The ester solvent can be reused after purification treatment in a recovery section. After the desolventization process, crude lithium bis(fluorosulfonyl)imide (a material β3) with a low water content (for example, less than 3000 ppm) is obtained. In the production of lithium bis(fluorosulfonyl)imide of the present application, a stage of alkalinization-dehydration-desolventization is called a β stage, and a specific process thereof can refer to a process flow chart in FIG. 2 of the present application.

Crystallization: crystallization means that when a material is in a non-equilibrium state, another phase will be precipitated, and the phase will be precipitated in the form of crystals. The material β3 is introduced into a crystallization kettle, and dichloromethane is added. Dichloromethane is used to dissolve the ester solvent instead of LiFSI, so that LiFSI is supersaturated and precipitated in the ester solvent, and crystal nuclei grow. A mixture obtained is introduced into a two-in-one device with filtering and washing functions to wash off other impurities attached to the surface of the LiFSI crystals. After a crystallization liquid is subjected to purification treatment in a recovery section, the ester solvent and the dichloromethane can be reused.

Drying: a washed material is introduced into a drying kettle. After heating a nitrogen gas, the nitrogen gas is introduced into the drying kettle. The material is fluidized under the action of stirring and airflow. In the large area of contact of gas and solid phases, water of the material evaporates rapidly, and the high-humidity nitrogen gas is discharged from the kettle to make the material meet drying requirements.

In some embodiments, the above crystallization and drying steps may not be performed, and the material β3 is directly put into a dissolution process.

Dissolution: in the dissolution process, an ester solvent such as ethyl methyl carbonate (EMC) or dimethyl carbonate (DMC) can be used for dissolution of the above dried crystals (in terms of the crystallization method) or crude product (in terms of the non-crystallization method), acid removal (if an HF content in a detected solution exceeds the standard (for example, a standard HF content is ≤50 μg/g), LiOH is used to remove acid), and water removal (if a water content in the detected solution exceeds the standard (for example, a standard water content is ≤20 μg/g) according to the needs. The solution is passed through a molecular sieve, concentrated, filtered by a filter element and stored (for example, in a bucket or a tank car).

The above is a general process for producing lithium bis(fluorosulfonyl)imide (LiFSI) in the present invention. In the process of synthesis and purification of LiFSI, a variety of reaction raw materials and processing aids are needed, such as triethylamine as a reactant and a solvent, an ester solvent (such as diethyl carbonate DEC) for a dehydration process, and dichloromethane (DCM) for a crystallization liquid, and various by-products and impurity ions are also produced, which are mainly $F^-$ produced by reaction 1 and an alkali metal fluoride obtained after the subsequent alkalinization process. These raw and auxiliary materials constitute a considerable part of costs of LiFSI production in the present invention, and thus need to be recycled and reused as much as possible, and due to environmental protection factors, the produced by-products and impurities also need to be treated and recycled as much as possible. On this basis, the inventors provide a method for recovering raw and auxiliary materials used in the production process. The method includes a plurality of different recovery sections, and these recovery sections are closely associated with and integrated into the process flow for producing LiFSI, so as to realize the separation and recovery of main raw and auxiliary materials in stages. A method for recovering raw and auxiliary materials in the production of lithium bis(fluorosulfonyl)imide will be described in detail below according to schematic process flow diagrams in recovery sections A-E in the accompanying drawings.

A recovery section A (α water alkalinization): a product mixture produced by reaction 1 in an a stage of LiFSI production is separated into an oil phase mainly including $(SO_2F—NH—SO_2F)\cdot Et_3N$ and an aqueous phase mainly including a triethylamine hydrogen fluoride salt and impurity ions. The separation of this step can be carried out by layering with a static mixer and a layered tank or by extraction with an extraction tower. Unexpectedly, it is found that when the product mixture of reaction 1 is extracted by the extraction tower, a content of an impurity ion (mainly $F^-$) in the obtained oil phase (a material α3, mainly including $(SO_2F—NH—SO_2F)\cdot Et_3N$) is significantly lower than that of the impurity ion in the oil phase obtained by the layering with the static mixer and the layered tank. In some embodiments, a content of an impurity ion in the oil phase obtained by layering with the static mixer is 5-30 times greater than the content of the impurity ion in the oil phase obtained by extraction with the extraction tower, optionally 10-20 times. In some embodiments, a concentration of $F^-$ in the oil phase obtained after extracting the product mixture through the extraction tower is 100-200 ppm, optionally 100-160 ppm. In contrast, a concentration of $F^-$ in the oil phase obtained by the layering of the static mixer and the layered tank can be as high as 1000-2000 ppm.

Figure 3:
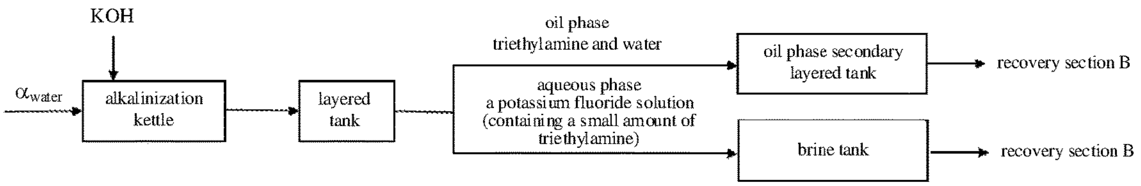
FIG. 3 is a schematic process flow diagram of a recovery section A (alkalinization of a water) in an embodiment of the present application.

The oil phase (the material α3) including $(SO_2F—NH—SO_2F)\cdot Et_3N$ is subjected to an alkalinization process according to reaction 2, and the aqueous phase (the material α water) including the triethylamine hydrogen fluoride salt and the impurity ions is introduced into an alkalinization kettle. Specifically, a certain amount of alkali metal hydroxide is added into the alkalinization kettle, α water is pumped according to a pH value, stirring is started, and the α water and the alkali metal hydroxide are mixed and react under stirring at normal temperature and pressure. The range of pH value may be selected in the range of 8-14, for example, 9-12. The reaction time may be 0.5-6 hours, optionally 1-4 hours. The alkali metal hydroxide may be selected from LiOH, NaOH or KOH, optionally, the alkali metal hydroxide is KOH. Then a solution obtained after the reaction in the alkalinization kettle is introduced into a layered tank for phase separation. For example, when the alkali metal hydroxide is KOH, KF generated is easily soluble in water. Since triethylamine and a KF aqueous solution have different densities and are immiscible, they can be separated by standing for layering. An upper layer oil phase is an organic phase including the triethylamine and part of the water, and is separated and stored in an oil phase secondary layered tank, and is subsequently combined with an oil phase material also including triethylamine and part of water obtained in a recovery section B. A lower layer is an aqueous phase mainly including an alkali metal fluoride solution, which may also include a small amount of triethylamine. The specific process flow of the recovery section A is shown in FIG. 3 of the present application.

A recovery section B (recovery of triethylamine): a product mixture obtained after the alkalinization reaction 2 in a β stage of LiFSI production is passed through an evaporator to remove the triethylamine and part of the water, and the evaporated triethylamine and water are introduced into a condenser for condensation and standing for liquid separation. Triethylamine is easily miscible with water at a temperature less than 18.5° C., and is slightly soluble in water at a temperature of 30° C.-55° C. By utilizing this characteristic, a mixed solution of the triethylamine and the water recovered by low-temperature condensation is heated to 30° C.-55° C., optionally 40° C.-45° C., and then stands for layering to remove water in the lower layer so as to achieve the goal of preliminary water removal.

An upper layer triethylamine solution obtained after the liquid separation is transferred to a triethylamine transfer tank, and is separated into an aqueous phase and an oil phase through a centrifuge. The centrifuge may be a disc centrifuge. The oil phase is an organic phase including water and triethylamine; and the organic phase and the organic phase containing the water and the triethylamine obtained in the recovery section A (stored in the oil phase secondary layered tank) are both introduced into a single-effect evaporation system for evaporation. The single-effect evaporation system may adopt a single-effect evaporator, and the required heating steam consumption can be calculated according to production flux and operation parameters. The single-effect evaporator refers to a single evaporator, and secondary steam generated during evaporation of a solution is no longer used. After evaporation, a water-containing triethylamine phase is obtained, and then remaining water is further removed by dehydration in a dehydration tower and rectification in a rectification tower respectively to finally obtain high-purity triethylamine. In some embodiments, the triethylamine obtained after rectification is introduced into a triethylamine blending tank for thorough stirring, and then stored in a triethylamine storage tank. In some embodiments, purity of the obtained high-purity triethylamine is above 95 wt %; optionally, the purity is above 98 wt %, above 99 wt % or above 99.5 wt %. The obtained triethylamine can be directly reused in the production of lithium bis(fluorosulfonyl)imide (LiFSI) of the present invention, for example, added to the reaction kettle of reaction 1, or transported to a special liquid packaging bucket or a tank car for external sales. Through the combination of the recovery section A and the recovery section B, the triethylamine used in the production of LiFSI can be recovered and reused in a high proportion, and the purity of the recovered triethylamine product is also high, which can significantly improve raw material utilization rate and economic efficiency in the production of LiFSI.

In some embodiments, the aqueous phase separated out by the centrifuge in the recovery section B is introduced into the alkalinization process of reaction 2 for alkali formulation, introduced into an extraction process as washing water, or introduced into a sewage treatment device for treatment. In the method of the present invention, materials used in each stage can be recovered and reused or post-treated, which can significantly improve environmental protection.

In some embodiments, a lower layer aqueous phase obtained by phase separation in the layered tank of the recovery section A mainly includes an alkali metal fluoride solution and a small amount of triethylamine; and a lower layer aqueous phase is obtained by evaporation in the single-effect evaporation system, the dehydration tower and the rectification tower in the recovery section B, and also mainly includes an alkali metal fluoride solution and a small amount of triethylamine. The two streams of materials are combined in a brine tank, and then a liquid in the brine tank is introduced into a stripping tower for stripping. By stripping, the liquid material can be divided into a light phase and a heavy phase. The light phase mainly includes triethylamine and water, which are condensed and recovered, and returned to the oil phase secondary layered tank of the recovery section A. The heavy component obtained after stripping is a salt-containing aqueous phase, and mainly includes an alkali metal fluoride solution. The heavy component is collected out of the bottom of the stripping tower, and introduced into a double-effect evaporator for evaporation, and evaporated water is condensed to obtain a high-concentration alkali metal fluoride solution. The double-effect evaporator connects two single-effect evaporators in series, uses secondary steam generated by a first-effect evaporator as a heating source, and introduces another effect evaporator; and as long as pressure and a boiling point of a solution in the evaporator are controlled to be properly reduced, the secondary steam generated by the first effect evaporator can be used for heating. In some embodiments, a concentration of the alkali metal fluoride solution can be increased from 25 wt % to more than 50 wt %, or even more than 55 wt %, by evaporation in the double effect evaporator. The obtained high-concentration alkali metal fluoride solution can be transported to a special liquid packaging bucket or a tank car for external sales.

In some embodiments, based on a difference in solubility of alkali metal fluoride at different temperatures, the alkali metal fluoride can be crystallized by cooling down in a crystallization kettle, and then the alkali metal fluoride can be extracted by centrifugation. An alkali metal may be Li, Na or K. Correspondingly, the alkali metal fluoride is LiF, NaF or KF.

Figure 4:
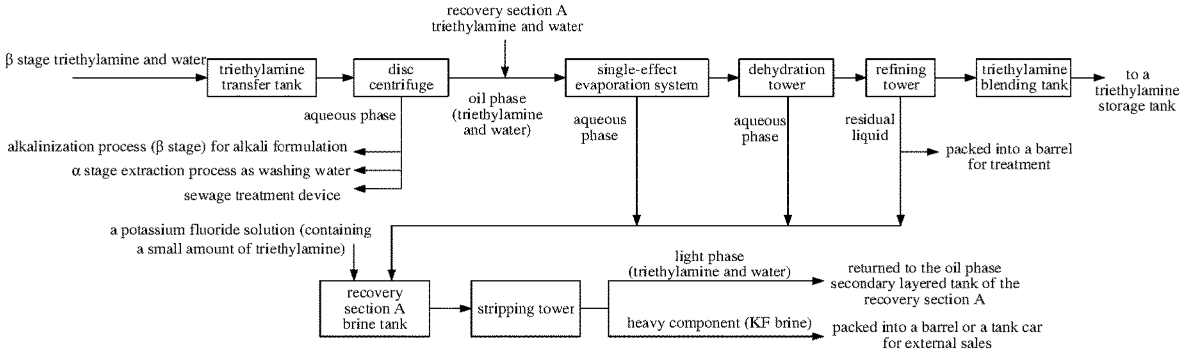
FIG. 4 is a schematic process flow diagram of a recovery section B (recovery of triethylamine) in an embodiment of the present application.

In some embodiments, the alkali metal fluoride is KF. By recovering the alkali metal fluoride, economic efficiency and environmental protection of LiFSI production can be further improved. The specific process flow of the recovery section B is shown in FIG. 4 of the present application.

Figure 5:
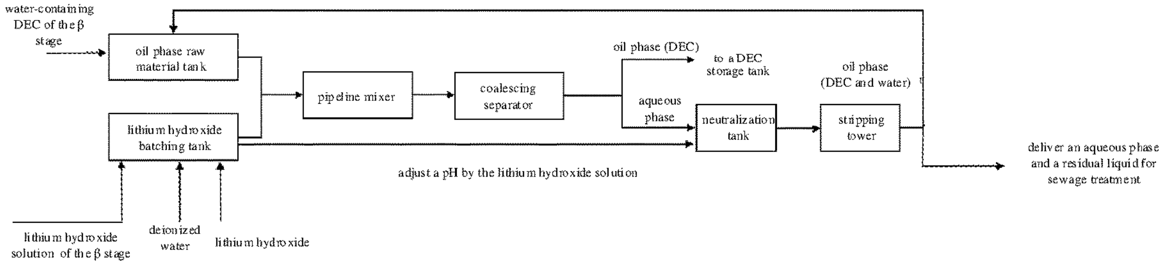
FIG. 5 is a schematic process flow diagram of a recovery section C (recovery of an ester solvent by an example of DEC) in an embodiment of the present application.

A recovery section C (recovery of an ester solvent): the R stage of the production of lithium bis(fluorosulfonyl)imide includes a dehydration process, in which an ester solvent is added to an evaporator to be mixed with the alkalinized reaction mixture from reaction 2, water is removed through evaporation of the ester solvent, and at the same time, a new ester solvent is continuously replenished, thereby achieving continuous water removal. The ester solvent may include, for example, ethyl methyl carbonate EMC, diethyl carbonate DEC, dimethyl carbonate DMC, and the like. The following uses diethyl carbonate DEC as an example to illustrate the recovering of ester solvent in detail. It can be understood that these descriptions are also applicable to other suitable ester solvents. Water-containing DEC evaporated from an evaporator is introduced into a condenser for condensation, and a condensate obtained is delivered into a condensate collection tank. The condensed water-containing DEC is pumped into a DEC buffer tank, mixed with a lithium hydroxide solution through a pipeline mixer, and then separated by a coalescing separator, to obtain an oil phase of DEC, and the oil phase is introduced into a DEC storage tank. The recovered DEC can be reused for the dehydration process (β stage). An aqueous phase obtained after the separation of the coalescing separator is introduced into a neutralization tank, and a lithium hydroxide solution is added to the tank to adjust a pH value. For example, the adjusted pH value may be 8-14, optionally 9-12. Then a material in the neutralization tank is introduced into a stripping tower through a preheater for stripping, to obtain an oil phase of water-containing DEC, which is returned to the DEC buffer tank; and an aqueous phase and a residual liquid obtained are introduced into a sewage treatment device for post-treatment. The lithium hydroxide solution introduced into the pipeline mixer to be mixed with the water-containing DEC may be obtained from the lithium hydroxide solution of the β stage, or by directly adding deionized water and lithium hydroxide, or from a mixture of the two. The lithium hydroxide solution may be pre-stored in a lithium hydroxide batching tank, and then introduced into the pipeline mixer to be mixed with the water-containing DEC. In addition, the lithium hydroxide solution may be directly pumped from the lithium hydroxide batching tank into the neutralization tank to adjust the pH value of the aqueous phase obtained after the separation of the coalescing separator. Purity of the DEC in a liquid stream introduced into the DEC storage tank may be above 95 wt %; optionally, the purity may be above 98 wt %, or above 99 wt %. The specific process flow of the recovery section C is shown in FIG. 5 of the present application, in which DEC is specifically used as an example of an ester solvent.

A recovery section D (recovery of a crystallization liquid): in the process of producing lithium bis(fluorosulfonyl) imide by a crystallization process, it is also necessary to recycle or reuse a used crystallization liquid. The main component of the used crystallization liquid is dichloromethane (DCM). Crude lithium bis(fluorosulfonyl)imide (a stream β3) that has been processed through a desolventization process is introduced into a crystallization kettle, and then the crystallization liquid dichloromethane is added. Dichloromethane is soluble in DEC instead of LiFSI, so that LiFSI is supersaturated and precipitated in DEC, and crystal nuclei grow. A mixture obtained is introduced into a two-in-one device with filtering and washing functions to wash off other impurities attached to the surface of LiFSI crystals. A water washing oil phase containing a crystallization liquid separated from the two-in-one device includes dichloromethane, water, an ester solvent and an impurity salt such as LiF. The water washing oil phase (dichloromethane, diethyl carbonate, water, salt, etc.) is pumped into a dehydration tower for dehydration. A condensate on the top of the tower is mainly dichloromethane and water, which is subjected to liquid separation treatment, and the separated water is collected in a sewage collection pool, and the separated dichloromethane all flows back to the tower. A tower bottom liquid of the dehydration tower is introduced into a single-effect evaporation system, a gas phase obtained by evaporation is introduced into a rectification tower for rectification, dichloromethane is obtained from a condensate on the top of the rectification tower and collected in a dichloromethane blending tank, lithium hydroxide is added to the tank, and a pH value is adjusted through a pump circulation pipeline and phases are separated, so that an aqueous phase obtained is separated for post-treatment, and an oil phase obtained is introduced into a dichloromethane storage tank. The recovered dichloromethane can be reused for the crystallization process.

Figure 6:
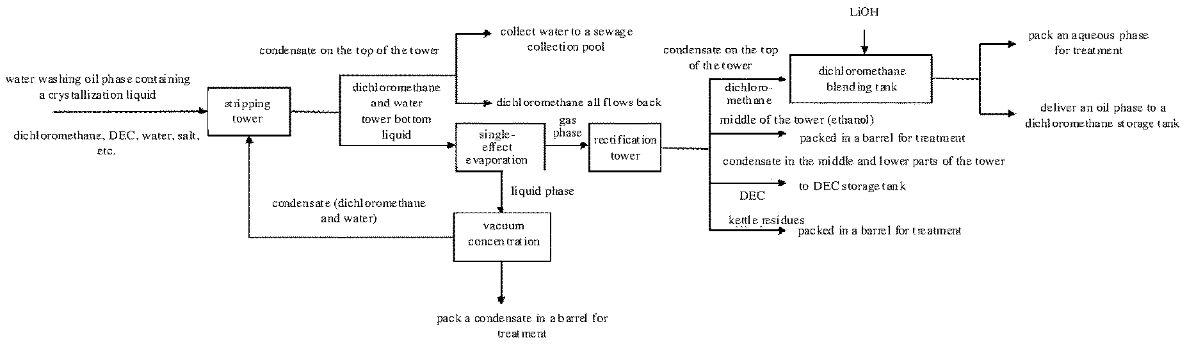
FIG. 6 is a schematic process flow diagram of a recovery section D (recovery of a crystallization liquid) in an embodiment of the present application.

In some embodiments, ethanol is separated from the middle of the rectification tower for post-treatment; an ester solvent is obtained from a condensate in the middle and lower parts of the rectification tower, and introduced into an ester solvent storage tank for reuse in the dehydration process; and a residual liquid obtained from the bottom of the rectification tower is separated for post-treatment. In some embodiments, a liquid phase obtained from the single-effect evaporation system is subjected to vacuum concentration, and a condensate obtained includes dichloromethane and an ester solvent, and is sent back to the dehydration tower; and the condensate obtained after vacuum concentration is separated for post-treatment. The specific process flow of the recovery section D is shown in FIG. 6 of the present application.

A recovery section E (recovery of a waste gas containing dichloromethane): dichloromethane is a volatile liquid. During the crystallization process and the subsequent crystallization liquid recovery process, due to temperature rise, a waste gas discharged from each stage contains a certain amount of dichloromethane. The dichloromethane discharged by means of the waste gas also needs centralized treatment and recovery. The waste gas containing dichloromethane from each process (such as the two-in-one device in the crystallization process, the dehydration tower and the rectification tower) is cooled and introduced into a third-stage adsorption resin for adsorption, and is desorbed by using steam after the adsorption is saturated, and then collected by condensation, and a liquid containing dichloromethane and water obtained by the collection is left to stand for layering. An upper layer aqueous phase contains a small amount of dichloromethane, and is separated as waste water for post-treatment; and a lower layer oil phase is dichloromethane containing a minute amount of water, and is introduced into a dehydration device for dehydration to a certain degree and then reused. The waste gas containing dichloromethane may be cooled by water at normal temperature. The third-stage adsorption resin may adopt a polar adsorption resin, for example, an adsorption resin with a polar functional group such as amide group, cyano group, and phenolic hydroxyl group.

Figure 7:
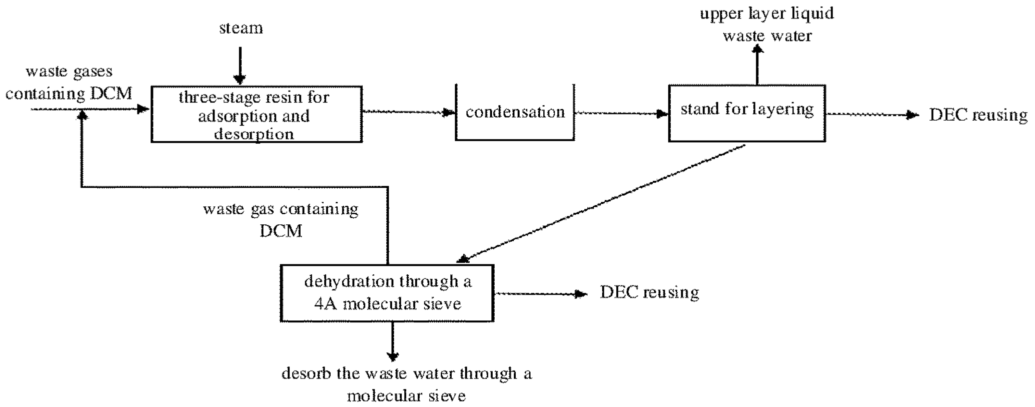
FIG. 7 is a schematic process flow diagram of a recovery section E (recovery of a waste gas containing dichloromethane) in an embodiment of the present application.

In some embodiments, the dehydration is performed through a 4A molecular sieve. The 4A molecular sieve has a pore diameter of 4A, and can absorb water molecules instead of dichloromethane, thereby realizing the dehydration of the oil phase of dichloromethane containing a minute amount of water. In some embodiments, a water content in the oil phase of dichloromethane containing the minute amount of water is 1000-2000 ppm, and the dehydration is performed until the water content is 50-200 ppm; optionally, the dehydration is performed until the water content is 50-100 ppm. The specific process flow of the recovery section E is shown in FIG. 7 of the present application.

The above is a flow of a method for recovering raw and auxiliary materials used in the production of lithium bis (fluorosulfonyl)imide (LiFSI) and performing post-treatment on three wastes generated through recovery sections A, B, C, D and/or E. It can be understood that these different sections may be freely combined with each other to realize the treatment of different target materials. In addition, each of the obtained target materials such as triethylamine or dichloromethane can be not only reused in the production of LiFSI, but also be made into a product that can be sold outside.

The method for recovering raw and auxiliary materials in the synthesis and purification process of lithium bis(fluorosulfonyl)imide (LiFSI) reduces production costs of LiFSI and reduces the generation of three wastes, so that the raw materials used are fully reused, and after a by-product is purified, additional economic benefits can also be generated.

Therefore, LiFSI is suitable for industrial production. By recovering and recycling the raw and auxiliary materials, consumption of the raw and auxiliary materials is reduced, utilization rate of reaction raw materials is improved, discharge and treatment costs of compounds are reduced, production costs are effectively reduced, and economic benefits are improved.

EXAMPLES

Examples of the present application will be described hereinafter. The examples described below are exemplary and merely used to explain the present application, and may not be understood as limitation to the present application. Where specific techniques or conditions are not specified in the examples, they are performed according to techniques or conditions described in the literature in the art or according to product specifications. Reagents or instruments used without specifying the manufacturer are all commercially available conventional products.

Example 1

1. Recovery of Triethylamine

40 $m^3$ of triethylamine and 35 $m^3$ of acetonitrile were respectively pumped into a 100 $m^3$ of synthesis kettle by a pump. Temperature of the kettle was reduced to 15° C., then 120 kg of ammonia gas was first introduced, and finally ammonia gas (2000 kg) and sulfuryl fluoride (26000 kg) were introduced simultaneously, while pressure in the kettle was maintained not greater than 0.4 MPa, and temperature in the kettle was maintained not greater than 15° C. After reaction lasted for 4 h, pressure in the kettle was reduced to 0.1 MPa, and stirring was stopped. A reaction mixture stream α1 obtained (containing 40 wt % of $(SO_2F—NH—SO_2F)·Et_3N$, 18 wt % of triethylamine hydrogen fluoride salt and 6 wt % of triethylamine) was filtered through a tetrafluoro filter bag with a pore diameter of 5 μm to filter out a solid by-product sulfonamide. A filtrate was pumped into a falling film evaporator (a temperature of a hot water bucket was 75° C.), and a solvent in the filtrate was evaporated under a vacuum degree of −0.02 MPa (a front stage of a vacuum pump was condensed with water at 0° C., and a latter stage was condensed with water at −15° C.) to obtain a stream α2 containing $(SO_2F—NH—SO_2F)·Et_3N$ and the triethylamine hydrogen fluoride salt (containing 70 wt % of $(SO_2F—NH—SO_2F)·Et_3N$ and 28 wt % of the triethylamine hydrogen fluoride salt) and a condensate containing acetonitrile. The condensate was recycled for synthesis in the synthesis kettle in the first step. The stream α2 was pumped to a rotary disc extraction tower (a stirring frequency was 15±1 Hz; and a flow rate was controlled so that deionized water to α2 is 1.2±0.1 (a weight ratio)), and was fully mixed with deionized water in the extraction tower (a mass ratio of the deionized water to the stream α2 was controlled to be 1.2:1 through a flowmeter) to obtain an aqueous phase α water containing the triethylamine hydrogen fluoride salt as an upper layer liquid (containing 77 wt % of the water and 22 wt % of the triethylamine hydrogen fluoride salt), and an oil phase α3 containing $(SO_2F—NH—SO_2F)·Et_3N$ as a lower layer liquid (still containing 15 wt % of the water). The lower layer oil phase α3 was delivered to an alkalinization step. Upon detection, the oil phase α3 still contained 100 ppm of $F^-$.

The upper layer aqueous phase α water was delivered to a recovery workshop for treatment (a recovery section A). In the recovery section A, a water was pumped into a 100 $m^3$ of alkalinization kettle and stirring was started. A potassium hydroxide solution (5 mol/L) was added into the alkalinization kettle, and a pH value of a liquid in the alkalinization kettle was adjusted to be maintained within the range of 8-10. After reaction lasted for 2 hours at normal temperature and pressure, a solution in the alkalinization kettle was pumped into a layered tank for 2 hours of phase separation. An aqueous phase was a potassium fluoride solution (containing a small amount of triethylamine), and was separated and pumped to a recovery section B; and an oil phase was an organic phase of water and triethylamine, and was separated and pumped to the recovery section B.

The oil phase α3 containing $(SO_2F—NH—SO_2F)·Et_3N$ was directly alkalinized in an evaporator B (a steam heating temperature of a hot water bucket was 35° C.), and a lithium hydroxide aqueous solution (with a concentration of 5 mol/L, where a volume ratio of the stream α3 to the lithium hydroxide aqueous solution was 1.1:1)) was added dropwise while stirring was performed continuously. After reaction lasted for 1 hour, a mixture stream β1-1 (a crude lithium salt) was obtained. Hot water at 35° C. was used for heating, and vacuum was activated to keep the vacuum degree in the kettle at −0.08 MPa, and steaming time was about 6 h. The front and latter stages of the vacuum pump performed five-stage condensation with water at 25° C. and 0° C. respectively. A condensate was left to stand for liquid separation. A lower layer liquid condensate water was reused for the alkalinization process to prepare a lithium hydroxide aqueous solution. Due to the decomposition of some products during the evaporation process, it needs to continuously add a lithium hydroxide aqueous solution (with a concentration of 5 mol/L) to maintain a pH at about 8. An upper layer liquid was a triethylamine aqueous solution and pumped to a recovery workshop for recovery (the recovery section B). In the recovery section B, the triethylamine aqueous solution was introduced into a triethylamine transfer tank, and was separated into an aqueous phase and an oil phase by a disc centrifuge. The oil phase was an organic phase containing water and triethylamine; the organic phase was combined with an organic phase containing water and triethylamine obtained in the recovery section A and introduced into a single-effect evaporator for evaporation to obtain a water-containing triethylamine phase. Then remaining water was removed by dehydration in a dehydration tower and rectification in a rectification tower respectively to obtain high-purity triethylamine. A recovery rate of recovered triethylamine was calculated as 93%, and purity was 99.2 wt % through quantitative analysis by gas chromatography. Chromatographic parameters were set as follows: column oven temperature: 40-260° C., detector type: FID/TCD, detector temperature: 300° C., air pressure: 0.4 MPa, hydrogen gas flow rate: 30 ml/min, and air flow rate: 400 ml/min.

2. Recovery of KF

A lower layer aqueous phase obtained by phase separation in the layered tank of the recovery section A mainly included a KF solution and a small amount of triethylamine. The lower layer aqueous phase was combined with a lower layer aqueous phase obtained in the single-effect evaporation system, the dehydration tower and the rectification tower in the recovery section B in a brine tank. After a liquid in the brine tank was introduced into a stripping tower for stripping, a light phase obtained mainly included triethylamine and water, and was returned to an oil phase secondary layered tank of the recovery section A; and a heavy component obtained after stripping mainly included the KF solution, and the heavy component was introduced into a double-effect evaporator for evaporation to obtain a high-concentration KF solution. A recovery rate of KF in the recovered high-concentration KF solution was 88%, and a concentration was 56.8 wt % through quantitative analysis by ion chromatography. Chromatographic parameters were set as follows: chromatographic column temperature: 30-45° C., detector: DS5 conductivity detector, analytical column: Shodex IC SI-90 4E, 4.6×250 mm, guard column: Shodex IC SI-90G, 4.6×10 mm, eluent flow rate: 1.0 mL/min, and regeneration solution flow rate: 1.0 mL/min.

3. Recovery of DEC

An aqueous solution of a product lithium bis(fluorosulfonyl)imide (referred to as β1-2) obtained after passing through the evaporator B was continued to be evaporated in a falling film evaporator C (a steam heating temperature of a hot water bucket was 50° C.). At the same time, diethyl carbonate (DEC) was metered and pumped (a flowmeter was controlled so that a volume ratio of DEC to the stream β1-2 was 0.6:1), vacuum (−0.08 MPa) heating and evaporation were continued, and the front and latter stages of the vacuum pump performed five-stage condensation with water at normal temperature and 0° C. respectively, and a condensate was an aqueous solution containing DEC. The aqueous solution containing DEC was stored in a collection tank and delivered to a recovery workshop for recovery (a recovery section C).

After evaporation in the falling film evaporator C, a stream β2 containing lithium bis(fluorosulfonyl)imide (containing 70 wt % of the lithium bis(fluorosulfonyl)imide, 29 wt % of diethyl carbonate and 1 wt % of the water) was obtained. During the evaporation in the falling film evaporator C, a lithium hydroxide aqueous solution (with a concentration of 5 mol/L) was metered and added to maintain a pH of the stream β2 at 8.

The stream obtained after evaporation by the falling film evaporator C was filtered to filter out a by-product lithium compound, so as to obtain a filtrate β2-1 containing 1 wt % of the water, 30 wt % of the diethyl carbonate and 69 wt % of the lithium bis(fluorosulfonyl)imide. The filtrate β2-1 was then pumped into a scraper evaporator D (a steam heating temperature of a hot water bucket was 75° C.), and vacuum (with a vacuum degree of −0.08 MPa) heating, evaporation and dehydration were continued. A condensate mainly contained DEC and a small amount of water, and the condensate was delivered to the recovery workshop for recovery (the recovery section C). After 6 hours of evaporation, lithium bis(fluorosulfonyl)imide β3 (containing 85 wt % of the lithium bis(fluorosulfonyl)imide and 15 wt % of the diethyl carbonate) with a water content of 3000 ppm was obtained.

In the recovery section C, the water-containing DEC was introduced into a DEC buffer tank, and mixed with a lithium hydroxide solution with a concentration of 50 wt % in a pipeline mixer, so that a pH value thereof was adjusted to 8-9. Then a mixed liquid stream was separated by a coalescing separator. An oil phase obtained after separation was mainly DEC, and was introduced into a DEC storage tank. Purity of DEC in a liquid material obtained in the DEC storage tank was 98.6 wt % through quantitative analysis by gas chromatography.

3. Recovery of a Crystallization Liquid

β3 was pumped to a crystallization kettle, and dichloromethane was pumped at a speed of 20 L/h. After stirring and mixing, β3 and the dichloromethane were pumped into a two-in-one device with filtering and washing functions, where the dichloromethane (containing DEC) was delivered to a recovery workshop for recovery (a recovery section D), and the remaining lithium bis(fluorosulfonyl)imide crystals fell into a drying kettle on the lower layer of the two-in-one device by gravity. Nitrogen gas was introduced in a drier to purge the crystals for drying, and drying temperature was 60° C. After drying and condensation, a condensate contained 99.5% dichloromethane and 0.5% water, and the condensate was delivered to a crystallization process for recycling and reusing. After a water content of the crystals dropped to a target limit (50 ppm), a powder product obtained was delivered to a dissolution section.

In the dissolution section, 70 L of ethyl methyl carbonate and 0.1 kg of lithium hydroxide were added to 30 kg of the lithium bis(fluorosulfonyl)imide β3. Then a disc centrifuge was used to perform centrifugation (with a rotation speed of 1500 rpm) to remove a solid, then a filtrate g-1 (HF is ≤50 μg/g) was delivered to a dehydration kettle in which 20 kg of molecular sieves were added, for stirring at a rotation speed of 800 rpm and treatment for 2 h. Then a filter was used to filter out the molecular sieves, and a filtrate g-2 (a water content is ≤20 μg/g) obtained was delivered to a product preparation kettle. Finally, demagnetization (performed by a demagnetization filter, 8000 gauss) and filtration (through a 1 micron filter, a 0.5 micron filter, and a 0.1 micron filter, respectively) were performed to obtain an ethyl methyl carbonate solution containing lithium bis(fluorosulfonyl)imide with a concentration of 28 wt %, and canning was performed finally.

In the recovery section D, a crystallization liquid washing oil phase (dichloromethane, DEC, water, a salt, etc.) was pumped into a dehydration tower for dehydration. A condensate on the top of the tower was mainly dichloromethane and water, and was subjected to liquid separation treatment, and the separated water was collected in a sewage collection pool, and the separated dichloromethane all flowed back to the tower. A tower bottom liquid of the dehydration tower was introduced into a single-effect evaporator, and a gas phase obtained by evaporation was introduced into a rectification tower for rectification, and dichloromethane was obtained from a condensate on the top of the rectification tower, and collected in a dichloromethane blending tank. A lithium hydroxide solution with a concentration of 50 wt % was added into the tank, to adjust a pH value to 9-10 through a pump circulation line and separate phases. An aqueous phase obtained was separated for post-treatment, and an oil phase obtained was introduced into a dichloromethane storage tank. Ethanol was extracted from the middle of the tower and packed into a barrel for treatment. DEC was extracted from the middle and lower part of the tower, and pumped to a DEC storage tank for reuse in a dehydration process (P stage). Kettle residues were packed into a barrel for treatment; a liquid phase through the single-effect evaporation was then subjected to vacuum concentration to further recover dichloromethane and diethyl carbonate DEC and sent back to the dehydration tower, and the concentrated liquid was packed into a barrel for treatment. Purity of dichloromethane in the oil phase introduced into the dichloromethane storage tank was 99.2 wt % through quantitative analysis by gas chromatography.

4. Recovery of a Waste Gas Containing Dichloromethane

A collection tube was used to collect a volatilized gas from the two-in-one device in the crystallization process and the top of the dehydration tower and rectification tower in the recovery section D. The gas mainly includes a waste gas containing dichloromethane and evaporated water. The collected waste gas was introduced into a dichloromethane absorption and recovery device, and was first cooled with water at normal temperature. After cooling, it was introduced into a third-stage adsorption resin for adsorption, and after the adsorption is saturated, steam was used for desorption. After condensation, collection was performed, and dichloromethane and water obtained by collection were left to stand for layering. An upper layer liquid water contained a minute amount of dichloromethane, and was used as waste water for post-treatment; and a lower layer liquid dichloromethane contained about 1800 ppm of water, and was pumped into a 4A molecular sieve dehydration device for dehydration to below 150 ppm and thus reused.

Example 2

Example 2 is carried out in the same way as Example 1, and differs in that in an a stage in which lithium bis (fluorosulfonyl)imide was produced, a stream α2 was transported by a pump to a static mixer (a ratio of length to pipe diameter L/D=10; and a flow rate is controlled so that deionized water to α2 is 1:1.2 (a weight ratio)) instead of an extraction tower to be fully mixed with the deionized water in the static mixer, and delivered to a layered tank to stand for layering for 2 h.

Finally, after a heavy component obtained in a stripping tower of a recovery section B was evaporated by a double-effect evaporator, a recovery rate of KF in a KF solution obtained was 79%, and a concentration was 42.8 wt % through quantitative analysis by ion chromatography.

Although the present application has been described with reference to embodiments, various modifications can be made and equivalents may be substituted for elements thereof without departing from the scope of the present application. In particular, as long as there is no structural conflict, various technical features mentioned in the various embodiments may be combined in any manner. The present application is not limited to the specific embodiments disclosed herein, and includes all technical solutions falling within the scope of the claims.

What is claimed is:

1. A method for recovering raw and auxiliary materials in production of lithium bis(fluorosulfonyl)imide, the production of lithium bis(fluorosulfonyl)imide comprising reaction 1 of subjecting sulfuryl fluoride, triethylamine and ammonia gas to reaction and subsequent reaction 2 of alkalinizing a reaction product, reaction 1

$$SO_2F_2 + NH_3 + Et_3N \longrightarrow (SO_2F-NH-SO_2F) \cdot Et_3N + Et_3N \cdot (HF)_n \quad (n=1\text{-}12),$$

and reaction 2

$$(SO_2F-NH-SO_2F) \cdot Et_3N + LiOH \longrightarrow (SO_2F-N-SO_2F)^-Li^+ + Et_3N + H_2O,$$

wherein the method comprises:

a recovery section A: separating a product mixture produced by reaction 1 into an oil phase comprising $(SO_2F-NH-SO_2F) \cdot Et_3N$ and an aqueous phase comprising a triethylamine hydrogen fluoride salt and impurity ions; subjecting the oil phase comprising $(SO_2F-NH-SO_2F) \cdot Et_3N$ to an alkalinization process according to reaction 2, and introducing the aqueous phase comprising the triethylamine hydrogen fluoride salt and the impurity ions into an alkalinization kettle to mix and react with an alkali metal hydroxide under stirring, and then introducing a solution obtained after reaction in the alkalinization kettle into a layered tank for phase separation, with an upper layer oil phase being an organic phase comprising water and triethylamine, which is separated out and stored in an oil phase secondary layered tank; and a recovery section B: passing a product mixture obtained by the alkalinization process according to reaction 2 through an evaporator to remove the triethylamine and part of the water, and introducing the evaporated triethylamine and water into a condenser for condensation and standing for liquid separation; transferring an upper layer triethylamine solution obtained after the liquid separation to a triethylamine transfer tank, to be separated into an aqueous phase and an oil phase through a centrifuge, the oil phase being an organic phase comprising water and triethylamine; introducing the organic phase and the organic phase comprising the water and the triethylamine obtained in the recovery section A together into a single-effect evaporation system to obtain a water-containing triethylamine phase; then removing remaining water by dehydration in a dehydration tower and rectification in a rectification tower respectively to obtain high-purity triethylamine.

2. The method according to claim 1, wherein purity of the high-purity triethylamine obtained by the method is above 95 wt %; optionally, the purity of the triethylamine is above 98 wt %, above 99 wt % or above 99.5 wt %.

3. The method according to claim 1, wherein the impurity ions comprise $F^-$, $SO_4^{2-}$, $FSO_3^-$, and $Cl^-$.

4. The method according to claim 1, wherein the product mixture obtained by the alkalinization process in the recovery section B is evaporated by the evaporator to obtain a mixture comprising triethylamine and water, and the mixture is condensed in a condenser, and then heated to a temperature of 30° C.-55° C., optionally 40° C.-45° C., to stand for layering.

5. The method according to claim 1, wherein the product mixture produced by the separation reaction 1 in the recovery section A is subjected to layering by a static mixer or extraction by an extraction tower.

6. The method according to claim 5, wherein a content of an impurity ion in the oil phase obtained by the layering with the static mixer is 5-30 times greater than the content of the impurity ion in the oil phase obtained by the extraction with the extraction tower, optionally 10-20 times; and optionally, the impurity ion is $F^-$.

7. The method according to claim 1, wherein the centrifuge is a disc centrifuge.

8. The method according to claim 1, wherein the aqueous phase separated out by the centrifuge in the recovery section B is introduced into the alkalinization process of reaction 2 for alkali formulation, introduced into an extraction process as washing water, or introduced into a sewage treatment device for treatment.

9. The method according to claim 1, wherein a lower layer aqueous phase obtained by phase separation in the layered tank of the recovery section A mainly comprises an alkali metal fluoride solution and a small amount of triethylamine, and is combined with a lower layer aqueous phase obtained in the single-effect evaporation system in a brine tank, the dehydration tower and the rectification tower in the recovery section B; after a liquid in the brine tank is introduced into a stripping tower for stripping, a light phase obtained mainly comprises triethylamine and water, which are returned to the oil phase secondary layered tank of the recovery section A; and a heavy component obtained after stripping mainly comprises the alkali metal fluoride solution, and the heavy component is introduced into a double-effect evaporator for evaporation to obtain a high-concentration alkali metal fluoride solution.

10. The method according to claim 1, wherein an alkali metal is Li, Na or K.

11. The method according to claim 1, wherein the production of lithium bis(fluorosulfonyl)imide further comprises a dehydration process performed by using an ester solvent, and a water-containing ester solvent obtained by evaporation and condensation is recovered by a recovery section C: introducing the water-containing ester solvent into an ester solvent buffer tank to be mixed with a lithium hydroxide solution in a pipeline mixer, and then separated by a coalescing separator, to obtain an oil phase of the ester solvent, and introducing the oil phase into an ester solvent storage tank.

12. The method according to claim 11, wherein an aqueous phase obtained after the separation of the coalescing separator is added with a lithium hydroxide solution to adjust a pH value, and then enters a stripping tower through a preheater for stripping, to obtain an oil phase of the water-containing ester solvent, which is returned to the ester solvent buffer tank; and an aqueous phase and a residual liquid obtained are introduced into a sewage treatment device for post-treatment.

13. The method according to claim 11, wherein the ester solvent comprises ethyl methyl carbonate EMC, diethyl carbonate DEC and dimethyl carbonate DMC.

14. The method according to claim 1, wherein the production of lithium bis(fluorosulfonyl)imide further comprises a crystallization process in which a crystallization liquid is used to dissolve an ester solvent and precipitate product LiFSI crystals, and a crystallization liquid washing oil phase obtained by evaporation and condensation comprises dichloromethane, an ester solvent, water and a salt; and the crystallization liquid is recovered by a recovery section D: introducing the crystallization liquid washing oil phase into a dehydration tower, wherein a condensate on the top of the tower comprises dichloromethane and water, and an upper layer aqueous phase after layering is introduced into a sewage collection tank for post-treatment, and a lower layer dichloromethane all flows back;

introducing a tower bottom liquid of the dehydration tower into a single-effect evaporation system, introducing a gas phase obtained by evaporation into a rectification tower for rectification, obtaining dichloromethane from a condensate on the top of the rectification tower, collecting the dichloromethane in a dichloromethane blending tank, adding lithium hydroxide to the tank, and adjusting a pH value through a pump circulation pipeline and separating phases, so that an aqueous phase obtained is separated for post-treatment, and an oil phase obtained is introduced into a dichloromethane storage tank.

15. The method according to claim 14, wherein ethanol is separated from the middle of the rectification tower for post-treatment; an ester solvent is obtained from a condensate in the middle and lower part of the rectification tower, and the ester solvent is introduced into an ester solvent storage tank for reuse in a dehydration process; and a residual liquid obtained from the bottom of the rectification tower is separated for post-treatment.

16. The method according to claim 14, wherein a liquid phase obtained from the single-effect evaporation system is subjected to vacuum concentration, and a condensate obtained comprises dichloromethane and an ester solvent, and is sent back to the dehydration tower; and the condensate obtained after vacuum concentration is separated for post-treatment.

17. The method according to claim 1, wherein the method further comprises a recovery section E for recovering a waste gas containing dichloromethane generated in each stage:

the recovery section E: cooling the waste gas containing dichloromethane generated in each stage to be introduced into a three-stage adsorption resin for adsorption, using steam for desorption after the adsorption is saturated, and then performing collection through condensation, wherein a liquid containing dichloromethane and water obtained by the collection is left to stand for layering, an upper layer aqueous phase contains a minute amount of dichloromethane, and is separated as waste water for post-treatment; and a lower layer oil phase is dichloromethane containing a minute amount of water, and is introduced into a dehydration device for dehydration and then reused.

18. The method according to claim 17, wherein a water content in the dichloromethane containing the minute amount of water is 1000-2000 ppm, and the dehydration is performed until the water content is 50-200 ppm.

19. The method according to claim 17, wherein the dehydration is performed through a 4A molecular sieve.

* * * * *